United States Patent [19]
Wood

[11] Patent Number: 5,590,764
[45] Date of Patent: *Jan. 7, 1997

[54] PACKAGE DISPENSER FOR PLURALITY OF GARMENTS

[76] Inventor: Frederick Wood, 3110 Devon Rd., Medford, N.Y. 11763

[*] Notice: The portion of the term of this patent subsequent to Dec. 14, 2010, has been disclaimed.

[21] Appl. No.: 514,699

[22] Filed: Aug. 14, 1995

Related U.S. Application Data

[63] Continuation of Ser. No. 229,639, Apr. 19, 1994, Pat. No. 5,456,354.

[51] Int. Cl.⁶ .......................... B65D 85/18; B65D 85/14; B65D 81/20; A47G 25/80
[52] U.S. Cl. .......................... 206/278; 206/69; 206/524.8; 223/111
[58] Field of Search .......................... 206/69, 278, 281, 206/524.8, 438; 223/111; 2/168

[56] References Cited

U.S. PATENT DOCUMENTS

| | | | |
|---|---|---|---|
| 3,282,414 | 11/1966 | Penksa | 206/438 X |
| 4,002,276 | 1/1977 | Poncy et al. | 223/111 |
| 4,069,913 | 1/1978 | Harrigan | 206/278 |
| 4,155,494 | 5/1979 | Poncy et al. | 223/111 |
| 4,159,069 | 6/1979 | Poncy et al. | 223/111 |
| 4,275,812 | 6/1981 | Poncy et al. | 206/278 |
| 4,696,065 | 9/1987 | Elenteny | 2/168 |
| 4,915,272 | 4/1990 | Vlock | 223/111 |
| 4,951,815 | 8/1990 | Ulbrich | 206/278 X |
| 5,269,405 | 12/1993 | Wood | 206/69 |
| 5,456,354 | 10/1995 | Wood | 206/278 |

*Primary Examiner*—Bryon P. Gehman
*Attorney, Agent, or Firm*—Kuhn and Muller

[57] ABSTRACT

A package dispenser for garments, such as latex surgical gloves is provided with an inner glove shape, which constricts the palms of a plurality of expandable, elastic gloves placed within each other, and forces the fingers of the gloves to expand and conform to a proper expanded position for insertion therein of the hand of a user into the innermost exposed glove of the plurality of gloves. The package sequentially dispenses one or more elastic expandable gloves, such as latex gloves. When a vacuum is drawn, the gloves are maintained in an open, expanded state, wherein the user loosely inserts a hand into the innermost glove of the plurality of gloves, breaks an air seal by pulling a tab, thus allowing air to leak in around the innermost glove, so that the glove snaps over the hand of the user in a tight fitting manner.

26 Claims, 7 Drawing Sheets

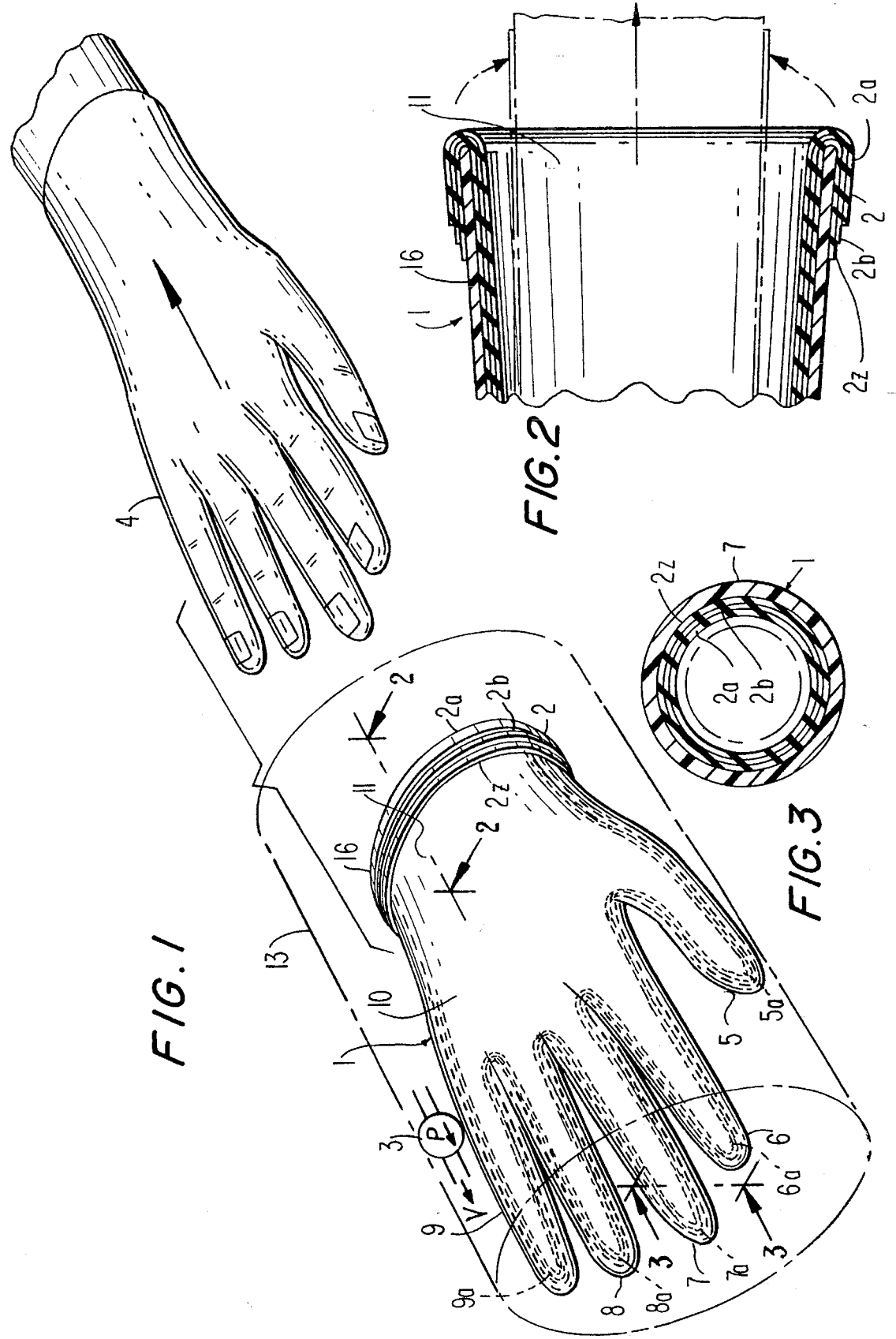

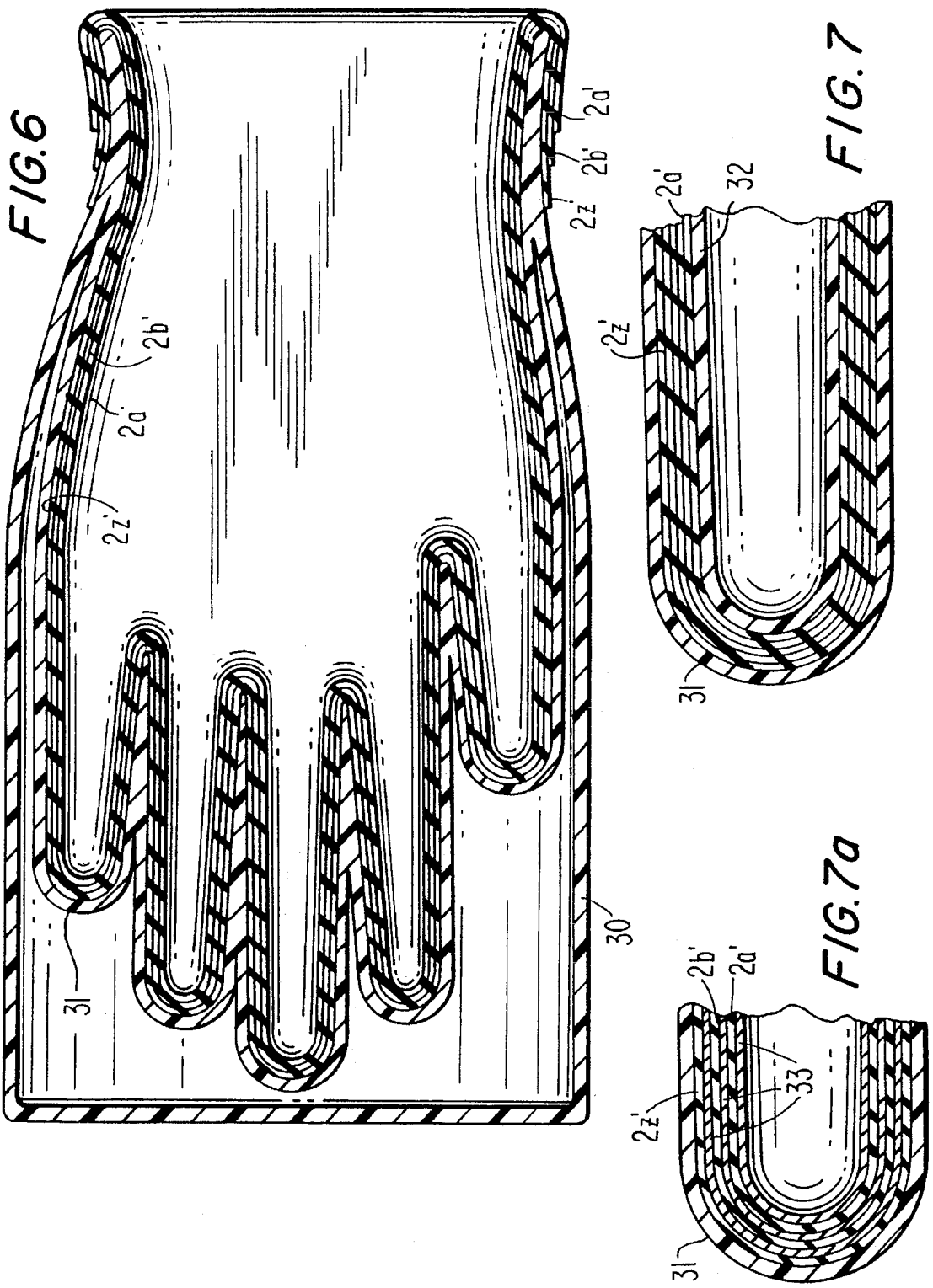

PACKAGE DISPENSER FOR PLURALITY OF GARMENTS

This application is a Rule 1.60 Continuation of application Ser. No. 08/229,639, filed Apr. 19, 1994, now U.S. Pat. No. 5,456,354.

FIELD OF THE INVENTION

The present invention relates to a package dispenser for a plurality of elastic expandable garments, such as latex gloves. More particularly, the package relates to a glove shaped package dispenser, wherein a user dons one or more gloves sequentially from a vacuum packed hand-shaped container.

BACKGROUND OF THE INVENTION

Various devices have been made for releasing a single glove from a vacuum chamber. Among these patents are U.S. Pat. No. 3,695,493 of Karr, disclosing an apparatus for alternately donning and removing a single glove within a vacuum chamber, U.S. Pat. No. 4,069,913 of Harrigan for a package for donning a single surgical glove, and U.S. Pat. No. 4,889,266 of Wight for an apparatus which removes a single glove from a disposable single use package.

Applicant's U.S. Pat. No. 5,269,405 discloses a container for sequentially dispensing a single glove from a plurality of gloves placed inside each other, wherein a vacuum holds the plurality of gloves intact in an open position for insertion of a hand therein. However, applicant's U.S. Pat. No. 5,269,405 does not describe a glove-shaped package, with individual finger portions, so that the five fingers can remain expanded or enlarged to allow the hand of the user to be loosely inserted, thereby obviating the need for powder as a lubricant to aid in sliding the glove on.

Other related patents include U.S. Pat. No. 685,574 of Conbole which shows a hand-shaped case, but for an unrelated use in mortuaries.

The patent to Breulis, U.S. Pat. No. 1,938,685 shows a somewhat bulb-shaped cavity for applying a surgical glove. The cuff of the glove is stretched over the opening of the cavity.

The patent to Violette, U.S. Pat. No. 2,741,410 shows a rack for removing gloves that may be wall mounted.

The patent to Smith, U.S. Pat. No. 2,886,8245 shows a rubber glove having a tapered wrist shape.

The patent to Schindler, U.S. Pat. No. 3,852,826 shows a surgical glove which is sterilized using radiation.

The patent to Stager, U.S. Pat. No. 4,186,445 shows a glove having a mylar outer coating and a polymer foam inner coating.

The U.S. Pat. No. 4,310,928 to Joung and U.S. Pat. No. 4,851,266 of Momose show talc free surgical gloves.

The patent to Elenteny, U.S. Pat. No. 4,696,065 shows a single peel-away multi-layer glove. No powder is used between the layers. This glove has a slight taper at the wrist portion.

The patent to Richardson, U.S. Pat. No. 5,224,221 describes a single glove which is two layers, one inside the other, with the space between them evacuated.

However, none of the above patents disclose an apparatus for donning one of a plurality of gloves within a glove-shaped vacuum chamber.

OBJECTS OF THE INVENTION

It is an object of the present invention to provide a glove package dispenser which has an inner shape which constricts the palm and forces the fingers of the glove to expand and conform to the proper position to allow easy donning.

It is therefore a further object of the present invention to provide a package dispenser for dispensing one or more gloves sequentially from a glove-shaped vacuum container.

It is yet another object of the present invention to provide a glove dispenser that allows powderless gloves to be easily donned.

It is a further object to provide a glove-shaped package with a releasing means including a thin continuous ribbon.

It is a still further object to provide a glove-shaped package with a releasing means including a thin ribbon for each glove.

It is yet another object to provide a glove package with an annular releasing means.

It is yet another object to provide a glove package with a releasing means including a tubular plastic cover which has a wasted area line cut spiraling around it so when the tab is removed it resembles a spiral shape.

It is yet another object to provide a container with a neck opening of the glove package which is tapered inward so that when the plastic is pulled off, the cuff of the glove easily rolls off the package and onto the hand.

It is a further object to provide a glove package dispenser in the shape of a large hand.

It is yet another object of the present invention to provide a glove dispenser for powder free gloves.

It is another object to provide a surgical glove package dispenser which provides a fast method of donning surgical gloves.

It is a further object to provide a surgical glove dispenser with a single wall container shaped like a large glove.

It is yet another object to provide a single or double walled glove package container with the inside shaped like a large glove and the outside having a box-like shape.

It is a further object to provide a glove package dispenser with a regular box-like shaped exterior and a flexible non-elastic large glove shape inside.

It is a further object to provide a glove package dispenser which is flattened for convenient storage and has a flexible non-elastic large glove shape inside.

It is yet another object to provide a glove package wherein the gloves in the package are stored in a relaxed shape, so that when the package is opened for use, the vacuum in the hollow tip causes a plurality of gloves to expand into the proper shape.

It is yet another object to provide a glove dispenser wherein an inner glove component which has holes in it to release trapped air.

It is yet another object to provide a glove dispenser which includes a flexible non-elastic glove shape on the inside of the plurality of gloves which is sealed within package in order to provide a leak-proof, air free area for increased shelf-life or storage life of the gloves.

It is yet another object to provide a leak-proof layer in between each glove.

It is yet another object to provide a plurality of gloves wherein there is provided an outermost glove shape which constitutes a leak-proof layer, for the purpose of shaping all the gloves.

It is yet another object to provide a glove package with an opening which is flared out to prevent unwanted releasing of the gloves.

It is yet another object to provide a glove dispenser package with an opening which is tapered in to aid in the releasing of each glove.

It is yet another object to provide a glove package with a mechanical attachment for pulling a release tab, to allow for hands-free or automatic releasing of the glove(s).

It is also an object of the present invention to improve over the disadvantages of the prior art.

SUMMARY OF THE INVENTION

In keeping with these objects and others which will become apparent, the present invention includes a garment-shaped container package dispenser for sequentially dispensing at least one elastic expandable garment, such as a glove of a plurality of gloves. In the preferred embodiment for gloves, such as latex surgical gloves or the like, the gloves are maintained in an open, expanded state, wherein the user loosely inserts a hand into the innermost glove, breaks the air seal by pulling a tab or similar device, thus allowing air to leak in around the innermost glove, so that the glove snaps over the hand of the user in a tight fitting manner.

The remaining gloves stay in an expanded state, so that if the user desires to wear two or more gloves, the user then releases a tab to break the seal against the next, exposed, innermost glove, whereupon the next innermost glove snaps into place over the previous first innermost glove upon the hand of the user.

The inside of the package dispenser container of the preferred embodiment for dispensing gloves is glove-shaped, so that the gloves may be expanded in the proper state and condition. Otherwise, in a non-descript tubular or box-like package, the finger portions will not expand or they will become distorted when forced to expand and will not be held in a useful shape, thus necessitating the use of powder to lubricate the finger portions.

In comparison, the glove-shaped package dispenser of the present invention permits proper expansion of all surfaces of the glove, including the fingers, thus obviating the need for powder as a lubricant.

To release a garment, such as a glove, the releasing means may be a thin continuous ribbon made out of latex or plastic, wherein the user pulls a predetermined length of the tab to release the innermost glove from the vacuum. Alternatively, the releasing means may be a tubular plastic cover, with a wasted line cut in an annular fashion, or spiraling around the cover, so that as it is removed the releasing means resembles a large spring or spiral shape. In this preferred embodiment, the neck of the hand-shaped glove package is tapered inward, so that when the plastic releasing means is pulled off, the cuff end of the innermost glove is separated from the package and onto the hand of the user.

With respect to the glove-shape of the glove package dispenser, several variations are described herein. For example, the inside and/or the outside of the package may be in the shape of a large glove.

Moreover, a conventional tubular or box-like package dispenser container may be used, wherein the inner glove-shape is achieved by having an outermost glove shape layer, made of a non-elastic plastic hand-shaped material, such as Mylar®.

The glove-shaped package dispenser container also allows the user to quickly put on the gloves in exigent circumstances, such as in an ambulance or for police use.

The glove-shaped package dispenser container, or similar modifications, obviates the need for powder to slide the glove on the hand of the user. The powder, which is presently used on latex gloves, causes problems, such as irritation of the eyes and skin. The powder may also cause allergic respiratory ailments. Moreover, hand perspiration causes the powder to become caked on, making it difficult to wash off. In addition, powder can contaminate surgical incisions, so a surgeon must carefully remove the powder with a sterile towel before surgery, which is a time consuming step.

In order to easily don gloves without powder, the glove-shape of the package dispenser constricts the palm portion of the glove and forces the fingers of the glove to expand and conform to the proper position to allow easy donning.

To release any trapped air, the inner glove shape mentioned in the above designs may have holes in it.

It is anticipated that the gloves are to be dispensed in disposable or refillable cartridges of a number of gloves, such as, for example, two dozen. The cartridges are held in a mounting means, such as upon a wall.

In order to hold the glove cartridge firmly in the holder the glove cartridge may have one or more female snaps on the top or one side of it which mate with male snaps on the inside of the glove cartridge holder. This allows for the recognition of different glove sizes and prevents the glove cartridges from being installed in a wrong location, thus, in turn, preventing the donning of the wrong sized glove upon the hand of the user.

In another embodiment for dispensing elastic expandable garments from a package, the package dispenser container of the present invention may also be used for donning condoms from a condom-shaped package which folds flat for storage. In the case of the condom package, where the garments would not be used up as fast as gloves, there may be a special leak-proof layer in between each condom. This would also provide extra cleanliness for the inside of the innermost condom that would otherwise be exposed to the outside air.

For non-surgical, non-elastic gloves, the gloves may be stacked and packaged without a vacuum if they are designed with a tapered shape so that the innermost glove(s) do not get crushed. These gloves have no air in between the layers. The wrist part of these gloves is the largest part, tapering down to the fingertips, wherein the gloves have an integral release tab which gets exposed only when the innermost glove inside of it has been removed.

In summary, the present invention relates to a package dispenser for a plurality of gloves. More particularly, the present invention relates to a glove-shaped package dispenser, wherein a user dons one or more gloves sequentially from a vacuum packed glove-shaped container. In a preferred embodiment, the shape of the package allows even powder free gloves to be donned quickly and easily, because the inner hand shape constricts the palm of the glove and forces the fingers to expand and conform to the proper position within the package interior.

DESCRIPTION OF THE DRAWINGS

The invention can best be understood from the specifications and drawings, in which:

FIG. 1 is a perspective view of one embodiment of the glove package dispenser of the present invention.

FIG. 2 is a blown-up cross-sectional view of the glove package dispenser as in FIG. 1, taken along line 2—2 of FIG. 1.

FIG. 3 is a blown-up cross-sectional view of the glove package dispenser as in FIG. 1, taken along line 3—3 of FIG. 1.

FIG. 6 is a side sectional view of a third embodiment of a glove package dispenser.

FIG. 7 is a blown-up sectional view of the glove package dispenser as in FIG. 6.

FIG. 7A is a blown-up sectional view of an alternate embodiment of the glove dispenser package.

DETAILED DESCRIPTION OF THE PREFERRED EMBODIMENTS

Figure 4:
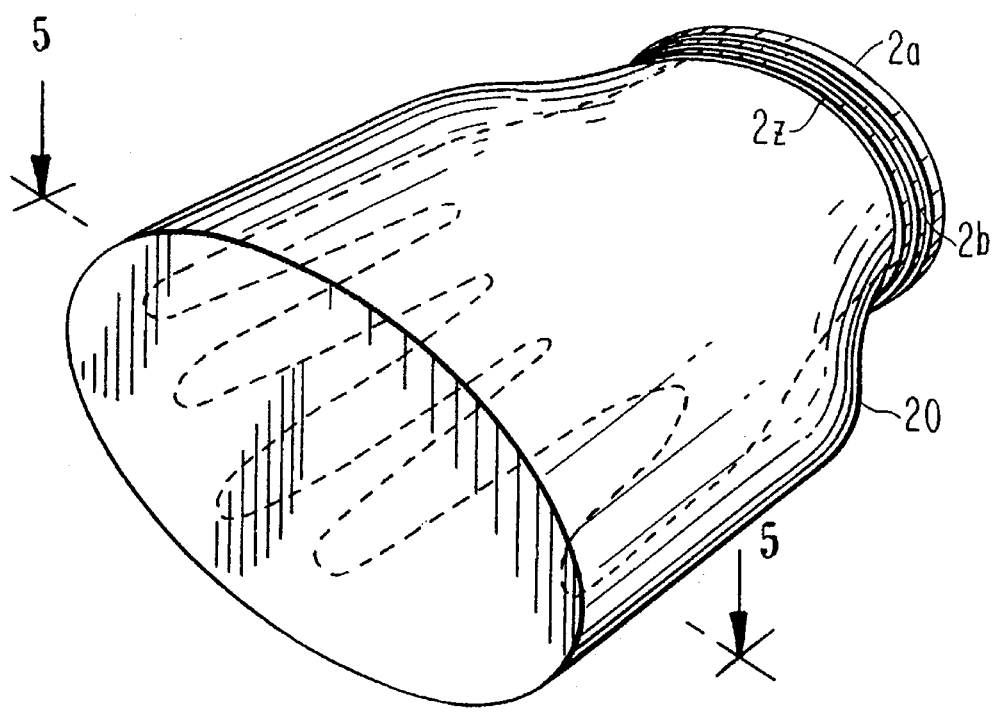
FIG. 4 is a perspective view of another embodiment of a glove package dispenser, wherein the inside surfaces of the package are a mirror image of a glove.

As shown in FIGS. 1–3, there is provided a package dispenser 1 for a plurality of elastic expandable garments such as gloves 2, for donning upon a hand of a person, wherein package dispenser 1 comprises a glove shaped inner cavity 11 within a housing 13 shown in phantom wherein a user inserts a hand and dons at least one glove 2 of a plurality of gloves 2a, 2b, 2c, 2d, . . . 2z etc. sequentially from a vacuum packed accumulation of garments 2, which is subject to a vacuum pressure V, within the dispenser such as drawn by a pump 3 in the manufacturing process for loading package dispenser 1 with gloves 2a, 2b, 2c, 2d, . . . 2z etc. The vacuum pressure V within the dispenser unit 1 is sufficient to open fully and expand uniformly each of the gloves in the glove-shaped cavity 11 within the dispenser 1.

In a preferred embodiment, the glove shape of package dispenser 1 eliminates the need for powder on gloves 2, such as, for example, latex surgical gloves. Vacuum V is drawn away from external outermost glove 2z and remaining gloves 2a, 2b, 2c etc., thus expanding gloves 2a, 2b, 2c, 2d . . . 2z in an open position.

Glove package dispenser 1 operates to release innermost single glove 2a from the application of vacuum V within package dispenser 1, which package dispenser 1 functions as an apparatus for sequentially donning one or more glove upon a body part such as a hand 4 from a plurality of gloves 2a, 2b, etc.

Glove package dispenser 1 enables the user to sequentially don gloves 2a, 2b, . . . 2z etc. from the plurality of gloves 2 placed inside each other, wherein vacuum V holds the plurality of gloves 2 within the cavity 11 intact in an open position for insertion of the user's hand 4 therein.

Glove-shaped package 1, includes palm portion 10 and individual finger portions 5, 6, 7, 8, 9 to maintain equal expansion of all surfaces of glove 2, so that, for example, five finger portions 5a, 6a, 7a, 8a, 9a of glove 2a are held in the proper expanded open position, thereby obviating the need for powder to lubricate gloves 2a, 2b, 2c etc.

The cuffs of the gloves 2a, 2b, 2c, 2d . . . 2z etc. are stretched over the collar portion 16 of the open end of the inner 11 cavity of the glove package dispenser 1 by virtue of which the open end of the gloves 2a, 2b, 2c . . . 2z etc. are maintained in an open, expanded state, permitting the user to insert a hand 4 into innermost glove 2a.

Figure 11:
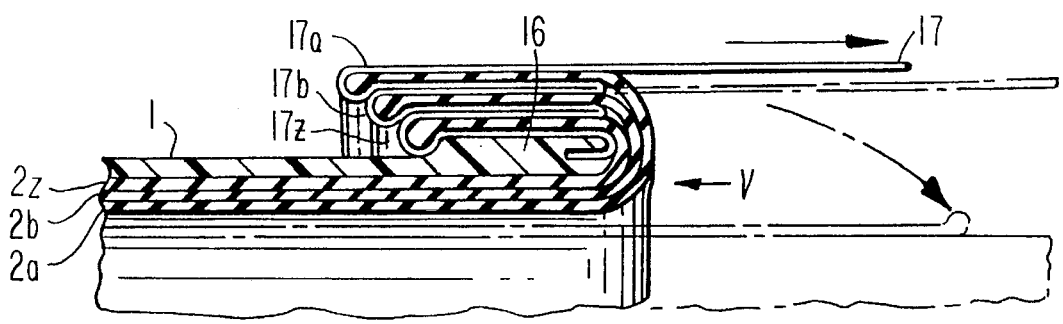
FIG. 11 is a blown-up sectional view of one embodiment for a release tab portion of the glove package dispenser.

As shown in FIG. 11, after insetion of a hand 4, the user breaks a seal by pulling a first portion 17a of seal tab 17 or similar device, such as a thin continuous ribbon made out of latex or plastic. The user pulls first portion 17a of a predetermined length of tab 17 to relieve innermost glove 2a from vacuum V, so that glove 2a is released from the next, subsequent innermost glove 2b, and glove 2a then snaps over the hand 4 of the user in an air tight manner.

Remaining gloves 2b, 2c, 2d . . . 2z etc. stay in an expanded state, so that if the user desires to wear two or more gloves 2 on one hand, the user then releases a further portion 17b of seal tab 17 from the next, exposed, innermost glove 2b, whereupon the next innermost glove 2b snaps into place over the previous first innermost glove 2a upon the hand 4 of the user. Ultimately, the user dons the remaining outermost glove 2z by pulling the last remaining portion 17z of release pull tab 17, to release outermost glove 2z from its open expanded state under the influence of vacuum V.

Figure 12:
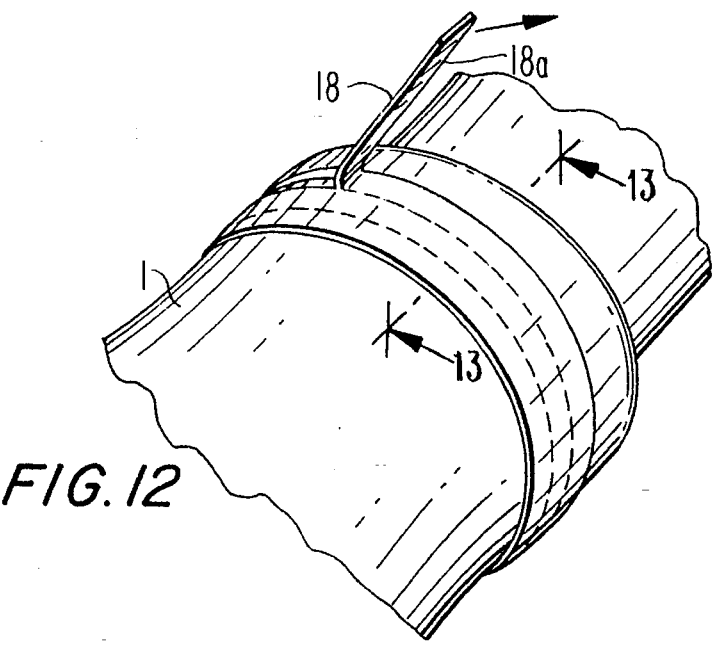
FIG. 12 is a blown-up perspective view of another embodiment for a release tab portion of the glove package dispenser.
Figure 13:
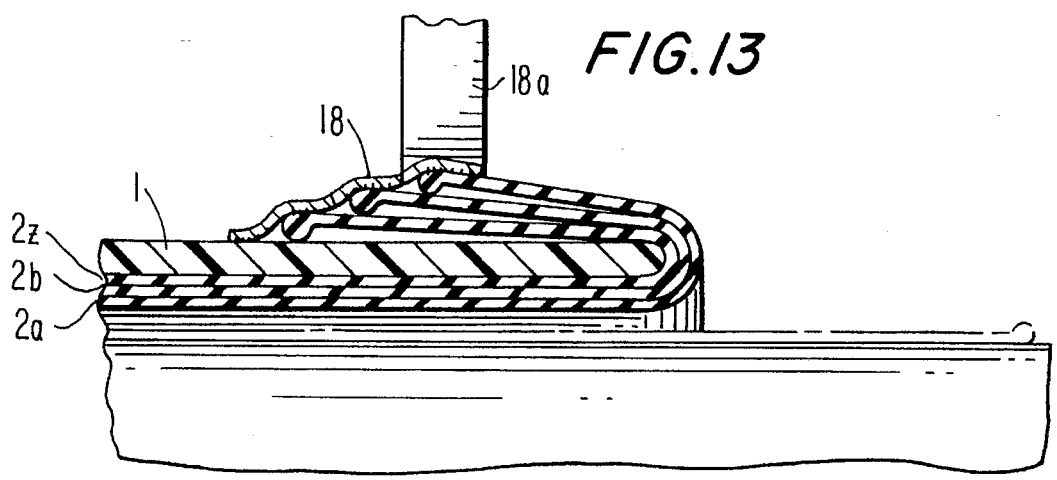
FIG. 13 is a blown-up cross-sectional view of the release tab as in FIG. 12, taken along lines 13—13 of FIG. 12.

In contrast to the release tab embodiment shown in FIG. 11, alternatively, as shown in FIGS. 12 and 13, the releasing means may be a tubular plastic cover 18, with a wasted linear area cut spiraling around the cover so that as it is removed, releasing portion 18a of release cover 18 resembles a large spring or spiral shape.

Glove package dispensing container 1 of the present invention is glove-shaped, to maintain equal expansion of all of the surfaces of gloves 2. Otherwise, in a non-descript tubular or box-like package, equal expansion is not maintained in the crevices and undulating finger portions 5, 6, 7, 8, 9 of glove 2, thus necessitating the use of powder to lubricate the finger portions and allow donning.

The glove-shaped dispenser package 1 of the present invention, as indicated, permits an equal expansion of all surfaces of glove 2, including palm portion 10 and finger portions 5, 6, 7, 8, 9, thus obviating the need for powder to lubricate the glove 2, to allow the user's hand to be readily inserted within the latex glove.

In one embodiment, collar neck 16 of the open end of the glove-shaped package dispenser 1 may be tapered inward, so that when the plastic releasing means 17 or 18 is pulled off, the cuff end of the innermost glove 2a is separated from the package 1 and onto the hand 4 of the user.

Figure 5:
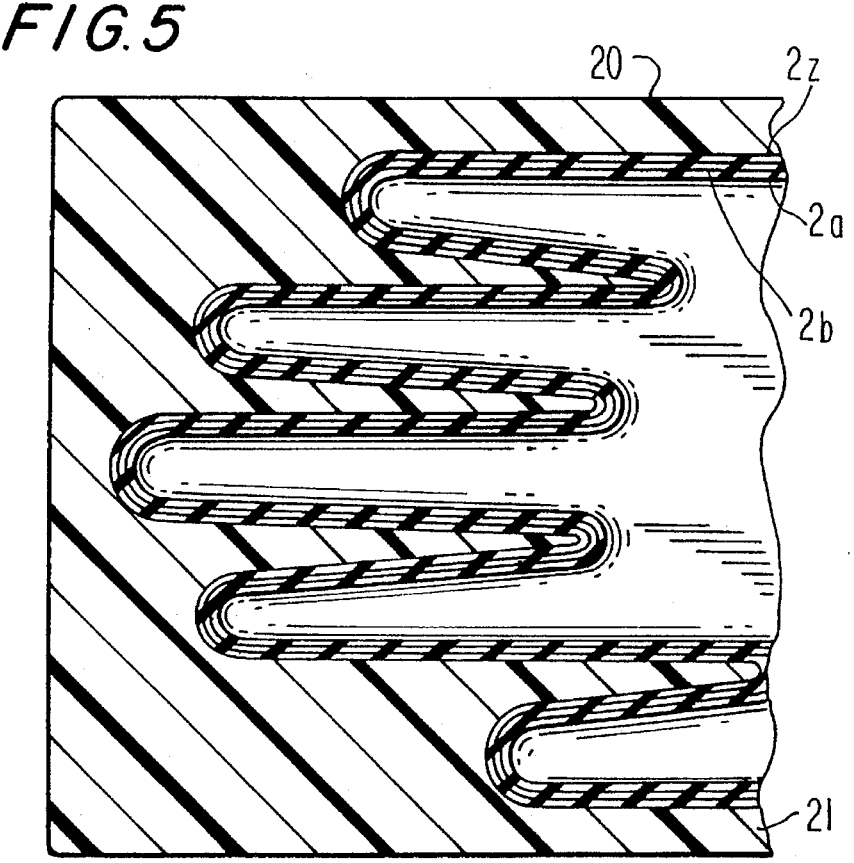
FIG. 5 is a blown-up cross-sectional view of the glove package dispenser as in FIG. 4, taken along lines 5—5 of FIG. 4.

With respect to the glove-shape feature of the glove package dispenser, several variations are described herein. For example, as shown in FIGS. 4 and 5, the inside 21 of a package 20 may be solid surrounding the shape of a large glove shaped cavity 11 with adequate means therein for drawing a vacuum.

Moreover, as shown in FIGS. 6 and 7, a conventional hollow container 30 may be used, such as a tubular container or a box-like container, wherein the glove-shape cavity 11 is achieved by having an outermost inelastic glove-like layer 31 positioned adjacent to and about outermost glove 2z' of gloves 2a', 2b' ... 2z', wherein inelastic layer 31 is made of an inelastic gas impermeable plastic hand-shaped material, such as non-elastic Mylar®.

Therefore, gloves 2a', 2b' ... 2z' will expand equally inside of each other in an expanded state against inelastic glove-like layer 31, due to the effect of vacuum V initiated by pump 3 (not shown) when gloves 2a', 2b, 2c' ... etc. 2z' are installed in an expanded state against inelastic gas impermeable layer 31 within container 30.

As shown in FIG. 7, if there is a significant time delay before innermost glove 2a' is used, a special preferably gas impermeable protective layer 32 is provided inside of innermost glove 2a'.

As shown in FIG. 7A an innermost protective layer 33 is provided inside innermost glove 2a'. Thereafter internal protective layers 33 preferably gas impermeable are provided between each glove of gloves 2a', 2b' ... 2z' until outermost glove shield layer 31 such as Mylar®.

In order to easily don gloves without powder, the glove-shape of the package 1 constricts palm portion 10 of each glove 2 and forces fingers 5, 6, 7, 8 and 9 of glove 2 to expand and conform to the proper position to allow easy donning upon the hand 4 of the user.

To release any trapped air, the inner glove shape mentioned in the above designs may have holes in it.

The gloves 2 are dispensed in disposable or refillable glove-shaped cartridges 1 including therein a plurality of gloves 2, such as two dozen. In use package dispenser cartridges 1 are held in a mounting means, such as upon a wall.

In order to hold glove cartridge package dispenser 1 firmly in a holder the glove dispenser cartridge 1 may have one or more female snaps located on the top or one side of the package dispenser which mate with male snaps on the inside of the glove cartridge holder. This allows for the recognition of different glove sizes and prevents the glove dispenser cartridges from being installed incorrectly.

Figure 8:
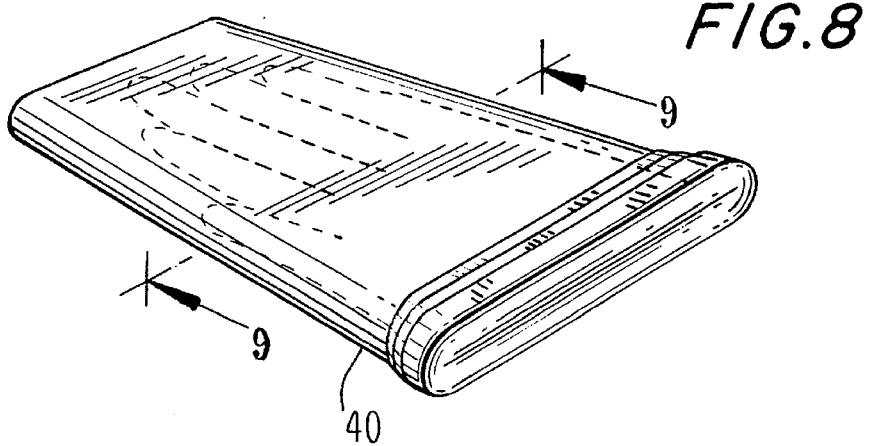
FIG. 8 is a perspective view of a fourth embodiment of a glove package dispenser, shown in a closed position.
Figure 9:
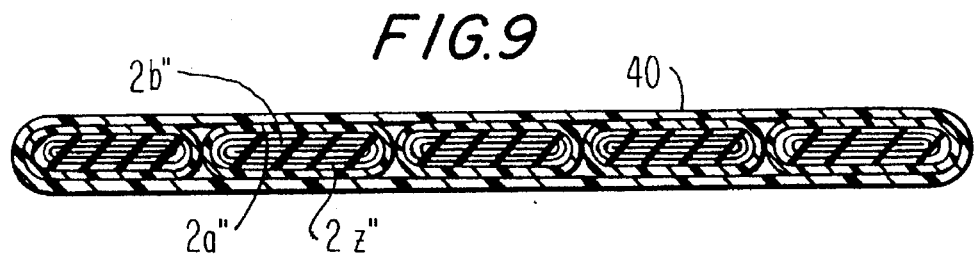
FIG. 9 is a blown-up cross-sectional view of the glove package dispenser as in FIG. 8, taken along lines 9—9 of FIG. 8.
Figure 10:
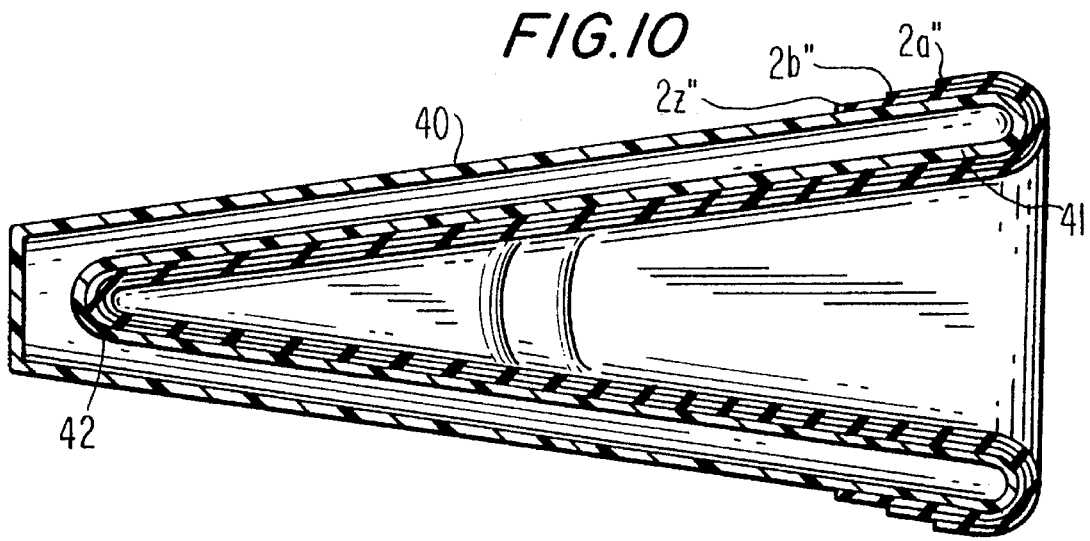
FIG. 10 is a blown-up cross-sectional side elevational view of the glove package dispenser as in FIG. 8, shown in an open position.

As shown in FIGS. 8–10, in an alternate embodiment of a package dispenser 40 for gloves 2a", 2b", 2c", 2d", etc., the gloves may be stacked and packaged within the dispenser package without a vacuum if they are designed with a tapered shape so that innermost gloves 2a", 2b", etc. do not get crushed. These gloves 2a", 2b", etc. have no air in between the layers. The wrist part 41 of these gloves 2a", 2b", etc. is the largest part, tapering down to the fingertips 42, wherein the gloves 2a", 2b", etc. have an integral release tab which is exposed only when the innermost glove inside of it has been removed.

Therefore, glove shaped package dispenser 1 allows a user to don one or more gloves sequentially from a vacuum packed hand-shaped container. In a preferred embodiment, the shape of the container will obviate the need for powder on latex gloves.

Figure 14:
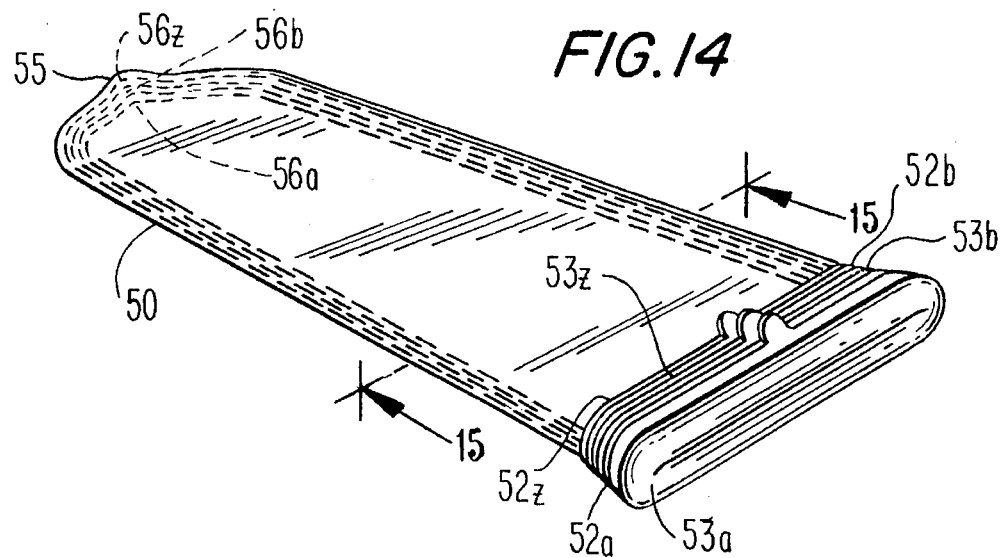
FIG. 14 is a perspective view of a condom dispenser embodiment of the present invention, shown in a closed position.
Figure 15:
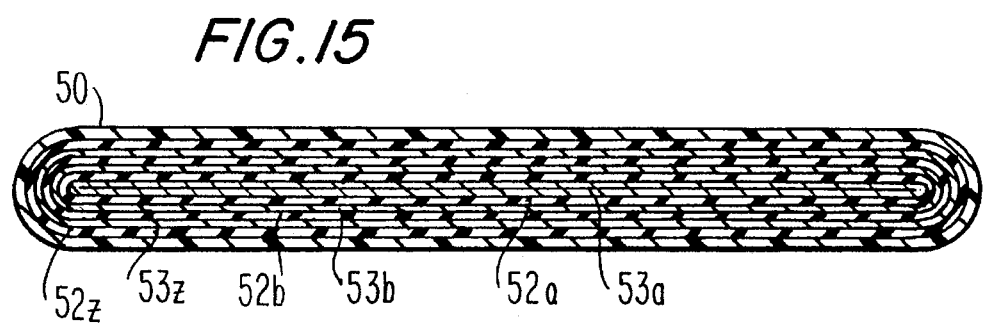
FIG. 15 is a blown-up cross-sectional view of the condom dispenser embodiment as in FIG. 14, taken along lines 15—15 of FIG. 14.
Figure 16:
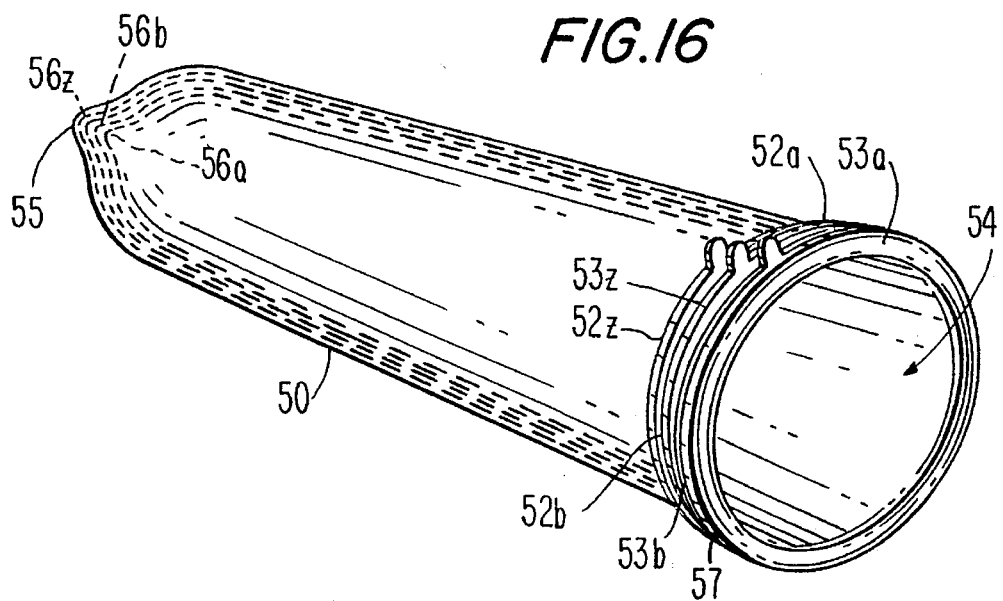
FIG. 16 is a perspective view of the condom dispenser embodiment as shown in FIG. 14, shown in an open position.

As shown in FIGS. 14–16, in another embodiment of the package dispenser for elastic, expandable garments, the container of the present invention may also be used for donning elastic, expandable condoms from a condom-shaped package 50, which folds flat for storage. In the case of condom package 50, where condoms 52a, 52b ... 52z etc. would not be used up as fast as gloves, there may be provided a special protective leak-proof layer 53a, 53b ... 53z inside of innermost condom 53a, and subsequent protective layers 53b ... 53z in between each of the condoms 52b ... 52z etc. This feature provides extra cleanliness for the inside of each condom 52a, 52b ... 52z etc.

Figure 17:
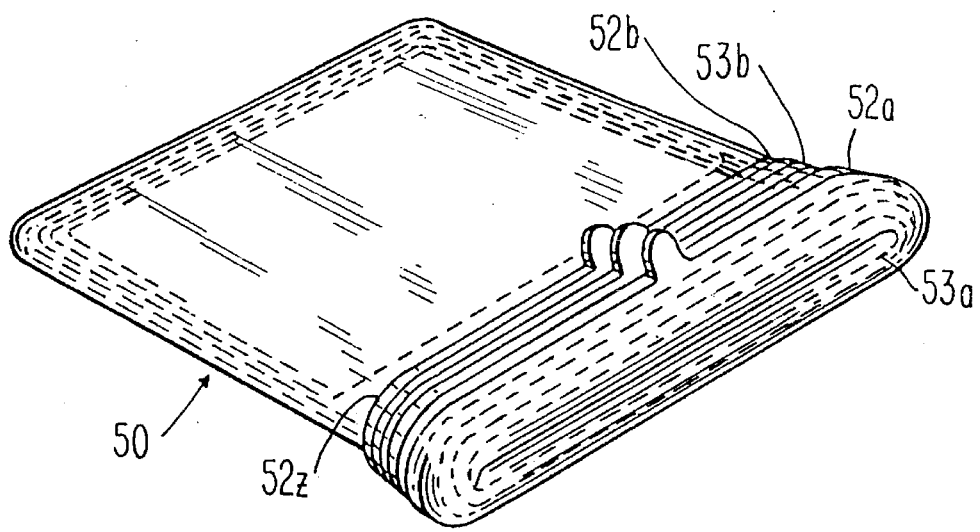
FIG. 17 is a perspective view of an alternate embodiment of a condom dispenser, shown in a closed position.
Figure 18:
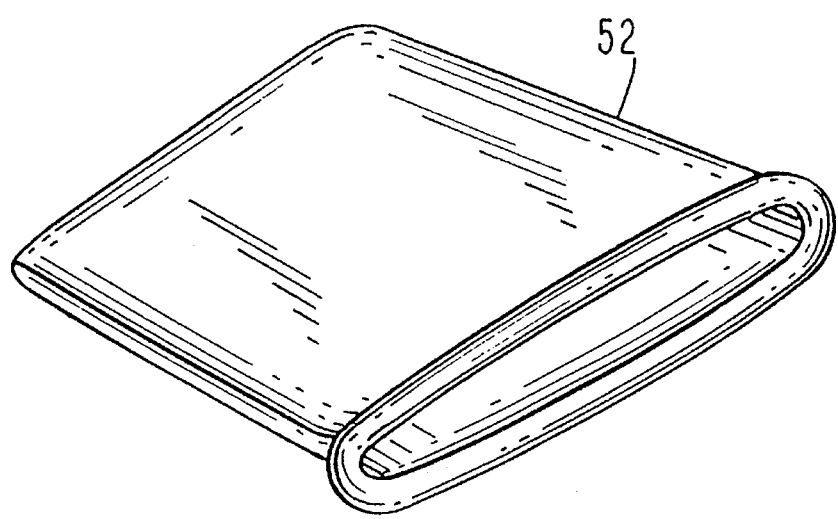
FIG. 18 is a perspective view of a condom within the condom dispenser as in FIG. 17.

For added convenience, as shown in FIGS. 17–18, condom package 50 may be short. In this case it would be used to dispense a rolled or folded condom 52a which would be unrolled or unfolded as needed.

In other respects, this further embodiment of the present invention for condoms differs only in that condom shaped package dispenser 50 is used, with or without a partially elongated receptacle tip end 55, depending upon the shape of each of condoms 52a, 52b ... 52z etc. Therefore, when condom package dispenser 50 is opened as shown in FIG. 16, condom package dispenser 50 maintains equal expansion of all surfaces of each of condoms 52a, 52b ... 52z etc, including partially elongated receptacle tips 56a, 56b ... 56z etc, so that innermost condom 52a can be held in the proper position for placement. The proximal open end portions 54 of the plurality of condoms 52a, 52b ... 52z are stretched over a collar portion 57 of condom package dispenser 50, and condoms 52a, 52b ... 52z etc. are maintained in an expanded state, wherein the user first removes innermost protective leak-proof layer 53a, thereby exposing innermost condom 52a, and inserts the penis into innermost condom 52a, and a release tab is pulled, so that condom 52a deflates over the skin in a tight fitting manner, leaving next a leak-proof layer 53b inside next innermost condom 52b.

Moreover, the inside shape of condom dispensing package 50 may be condom shaped, or the plurality of condoms may be inserted in an outermost condom shaped layer made of a non-elastic material, such as Mylar®, similar to the glove embodiment described in FIGS. 6 and 7.

It is further noted that other modifications may be made to the present invention, without departing from the spirit and scope of the present invention, as noted in the appended claims:

What is claimed is:

1. A package dispenser for the dispensing of a plurality of garments made of an elastic, expandable material for wear upon a body part, each of said garments having a distal closed end and an open end for insertion of the body part therein, wherein a vacuum is drawn from the elastic expandable material around the body part in order to expand the elastic expandable material in an open position for insertion of the body part therein to obtain an external protection over the body part, said package dispenser comprising:

a container, said container having a housing, said housing having a cavity therein, said cavity of said container having therein said plurality of the garments, each garment except an outermost garment of said plurality of garments being fitted inside of another of said garments;

said container having an open end, said open end of each of said garments being wrapped around said open end of said container, said plurality of garments covering said open end of said container from said distal closed end;

said plurality of garments being wrapped in a predetermined pattern so that an innermost garment is exposed to said open end of said container, and next subsequent garments of said plurality of garments being wrapped around said innermost garment;

said garments having an outermost garment enclosing said next subsequent garments and said innermost garment; and, said container having an outside layer and an inelastic, gas-impermeable inside layer, said inelastic, gas-impermeable inside layer having a geometric shape conforming to a geometric shape of said outermost garment, wherein a vacuum is applied between said outermost garment and said inelastic gas-impermeable inside layer of said container for expansion of said garments in an open position against said inelastic, gas-impermeable inner layer in an expanded position for insertion of the body part therein upon release of the vacuum against said innermost garment, said innermost garment being collapsible onto said body part.

2. The package dispenser for dispensing of garments as in claim 1, further comprising said container having two accesses, one access being located in said open end of said container for an insertion of the body part therein and another access being located in said distal closed end for evacuation of air.

3. The package dispenser for the dispensing of garments as in claim 1, further comprising said inelastic, gas-impermeable inner layer of said container being made in the shape of a glove for dispensing said innermost glove therefrom upon a hand.

4. The package dispenser for the dispensing of garments as in claim 1, wherein said package dispenser is a condom dispensing package dispenser including a plurality of condoms, and wherein said inelastic, gas-impermeable innerlayer of said container is made in the shape of a condom, said package dispenser dispensing an innermost condom of said plurality of condoms therefrom upon a penis.

5. The package dispenser as in claim 4, further comprising at least one leak-proof layer positioned in between each adjacent condom of said plurality of condoms.

6. The package dispenser for the dispensing of garments as in claim 1, further comprising said container having a movable releasing means for producing the displacement of said innermost garment from the package dispenser.

7. The package dispenser as in claim 6, wherein said releasing means includes a thin continuous ribbon.

8. The package dispenser as in claim 6, wherein said releasing means is annular.

9. The package dispenser as in claim 6, wherein said releasing means includes a tubular plastic cover including a wasted area line cut spiraling around said package dispenser.

10. The package dispenser for dispensing of garments as in claim 1, wherein a user dons said at least one garment sequentially from a vacuum packed container having a shape conforming to a shape of said innermost garment, each of said garments further having a palm portion and a plurality of finger portions, said container having a means for constricting said palm portion of said innermost garment and for forcing said finger portions of said innermost garment to expand and conform to the proper position to allow easy donning, said means comprising said inelastic, gas-impermeable inner layer of said container being glove-shaped.

11. The package dispenser as in claim 10, further comprising a neck collar at said open end of said package dispenser, said collar being tapered inward.

12. The package dispenser as in claim 10, further comprising a neck collar located at said open end of said package dispenser, said collar being flared outward.

13. The package dispenser as in claim 1, further comprising said container having an inside shaped like a large glove and an outside having a predetermined shape.

14. The package dispenser as in claim 1, further comprising said package dispenser having a exterior of a predetermined shape and a flexible non-elastic large glove shaped member inside.

15. The package dispenser as in claim 1, wherein said package dispenser is flattened and said package dispenser has a flexible non-elastic large glove shaped member inside.

16. The package dispenser as in claim 1, wherein said garments in said package dispenser are stored in a relaxed shape, so that when the package dispenser is opened for use, a vacuum in said package dispenser causes a plurality of garments to expand into the proper shape.

17. A container sequentially dispensing an innermost glove from a plurality of gloves placed inside each other, wherein a vacuum holds said innermost glove of said plurality of gloves intact in an open expanded position for insertion of a hand therein, said container being glove-shaped package having a plurality of individual finger portions so that the five fingers of said innermost glove can remain expanded to allow the hand of a user to be loosely inserted therein, said innermost glove having a cuff, said cuff of said innermost glove being stretchable over an open end of said container, said innermost glove being inside another subsequent glove of said plurality of gloves, wherein a releasing means is provided for producing a space between said innermost glove and said another subsequent glove.

18. The package dispenser as in claim 17 being mountable upon a wall, said container having a mateable fastener mateable with a mounting means upon the wall.

19. A glove-shaped container package dispenser for sequentially dispensing at least one glove of a plurality of gloves, said package dispenser further comprising a plurality of air seals, said plurality of gloves being maintained in an open, sealed expanded state, wherein a user loosely inserts a hand into an innermost glove of said plurality of gloves, a means for breaking an innermost air seal of said plurality of air seals, said means comprising a pull tab, said means allowing air to leak in around said innermost glove of said plurality of gloves, so that the glove snaps over the hand of the user in a tight fitting manner, wherein the remaining gloves of said plurality of gloves stay in an expanded state, so that if a user desires to wear two or more gloves, the user then breaks a next subsequent seal for a next, exposed, innermost glove, whereupon said next innermost glove snaps into place after being released from a next subsequent seal, over the previous first innermost glove upon the hand of the user, said container having an inside being hand-shaped responsive to holding said gloves in an expanded state.

20. A package dispenser for dispensing of garments for wear upon a body part, said garments having a distal closed end and an open end for insertion of the body part therein, said package dispenser comprising:

a container housing having an inner cavity, said inner cavity having a plurality of garments therein, each of said garments wrapped inside of each other of said garments, each of said garments having a predetermined geometric shape;

said container having an inner shaped layer conforming to said predetermined geometric shape of each of said garments;

said plurality of garments being assembled in a predetermined pattern so that an innermost garment is exposed to said open end of said container, and subsequent garments of said plurality of garments being wrapped around said innermost garment;

said garments being tapered from each said open end of each of said garments toward each said distal closed end of each of said garments; and, a tab responsive to releasing said innermost, tapered garment from said plurality of garments upon release of said tab.

21. The package dispenser as in claim 20, wherein said inner layer has holes therein to release trapped air.

22. A package dispenser for dispensing of a plurality of condoms made of an elastic, expandable material for wear upon a body part, each of said condoms of said plurality of condoms having a distal closed end and an open end for insertion of the body part therein, said package dispenser comprising:

a container, said container having a cavity therein, said cavity of said container having therein said plurality of condoms, all but the outermost condom being fitted inside of another of said condoms, said container having an open end, said open end of each of said condoms being rolled around said open end of said container, said plurality of condoms covering said open end of said container;

said plurality of condoms being wrapped in a predetermined pattern wherein an innermost condom is exposed to said open end of said container, and next condoms of said plurality of condoms are wrapped around said innermost condom;

said plurality of condoms having an outermost condom enclosing said next condoms and said innermost condom; said innermost condom having an outer sealed layer between said open end of said container and said innermost condom, each next condom having a further sealed layer, said further sealed layer having a geometric shape generally conforming to a geometric shape of said outermost condom.

23. The package dispenser as in claim 22, wherein said container is flattened in a closed position and openable to an open expanded position for insertion of the body part therein.

24. The package dispenser for the dispensing of condoms as in claim 22, further comprising said container having a movable releasing means for producing the displacement of said innermost condom from said condoms.

25. The package dispenser as in claim 22 wherein each outer sealed layer and said further sealed layers comprise an impermeable barrier material.

26. A package dispenser for dispensing of condoms for wear upon a body part, said condoms having a distal closed end and an open end for insertion of the body part therein, said package dispenser comprising:

a container having an inner cavity, said inner cavity having a plurality of condoms, each said condom wrapped inside of each other of said condoms, each of said condoms having a predetermined geometric shape;

said container having a plurality of sealed layers conforming to said predetermined geometric shape of each of said condoms;

said condoms being in a predetermined pattern wherein an innermost condom is exposed to said open end of said container, a first sealed layer being provided between said innermost condom and said open end of said container, and each next condom of said plurality of condoms is rolled around said innermost condom; and, a tab responsive to releasing each of said condom from said plurality of condoms upon release of said tab.

\* \* \* \* \*